United States Patent [19]

Kohayakawa

[11] Patent Number: 5,371,558

[45] Date of Patent: Dec. 6, 1994

[54] OPHTHALMIC APPARATUS

[75] Inventor: Yoshimi Kohayakawa, Yokohama, Japan

[73] Assignee: Canon Kabushiki Kaisha, Tokyo, Japan

[21] Appl. No.: 99,397

[22] Filed: Jul. 30, 1993

Related U.S. Application Data

[63] Continuation of Ser. No. 846,777, Mar. 9, 1992, abandoned, which is a continuation of Ser. No. 535,137, Jun. 8, 1990, abandoned.

[30] Foreign Application Priority Data

Jun. 13, 1989 [JP] Japan .................. 1-150815

[51] Int. Cl.$^5$ .................................. A61B 3/14
[52] U.S. Cl. .................. 351/208; 351/206; 351/211
[58] Field of Search ............ 351/206, 207, 208, 211, 351/221; 354/62

[56] References Cited

U.S. PATENT DOCUMENTS

| | | |
|---|---|---|
| 4,252,420 | 2/1981 | Kohayakawa . |
| 4,293,198 | 10/1981 | Kohayakawa et al. . |
| 4,452,517 | 6/1984 | Kohayakawa . |
| 4,607,922 | 8/1986 | Humphrey .......... 351/208 |
| 4,715,703 | 12/1987 | Cornsweet et al. ...... 357/208 X |
| 4,820,037 | 4/1989 | Kohayakawa et al. . |

Primary Examiner—William L. Sikes
Assistant Examiner—Hung Xuan Dang
Attorney, Agent, or Firm—Fitzpatrick, Cella, Harper & Scinto

[57] ABSTRACT

An ophthalmic apparatus provided with an alignment unit for projecting onto a light position detecting sensor the surface of the front eye part of one of an examinee's eyes looking into binocular openings which is opposed to an eye examining system for detecting the information of an eye to be examined, and effecting the alignment of the eye examining system to the eye to be examined on the basis of the light position output of the sensor.

30 Claims, 3 Drawing Sheets

OPHTHALMIC APPARATUS

This application is a continuation of application Ser. No. 07/846,777 filed Mar. 9, 1992, now abandoned, which is a continuation of application Ser. No. 07/535,137, filed Jun. 8, 1990, now abandoned.

BACKGROUND OF THE INVENTION

1. Field of the Invention

This invention relates to an ophthalmic apparatus, for example, an eye-refractometer, used for example in ophthalmic hospitals and capable of automatically effecting alignment.

2. Related Background Art

In an eye-refractometer according to the prior art, a face pad portion is generally provided with a chin pad and a forehead pad, and alignment for accurately projecting a light beam for measuring the refractive value onto an eye to be examined is accomplished by the examiner vertically adjusting the chin pad in accord with the examinee's face portion, and adjusting the position of the entire apparatus including an eye examining system by means of a sliding stand so that the projected position of the light beam may coincide with the eye to be examined while observing the front eye part of the eye to be examined through a monitor. An apparatus is also known in which rough adjustment is manually effected and fine adjustment is automatically effected to thereby accomplish alignment.

However, in the example of the prior art having the above-described construction, all the process of alignment are not automated and therefore in at least a part of the process, for example, the aforementioned rough adjustment, measurement of the refractive value cannot be accomplished unless the examiner operates an eye-refractometer.

SUMMARY OF THE INVENTION

It is an object of the present invention to provide an ophthalmic apparatus in which the position of an eye to be examined is made substantially constant irrespective of the size of an examinee's face and alignment can be accomplished quickly.

It is also an object of the present invention to provide an ophthalmic apparatus such as an eye-refractometer in which the entire process of alignment is automated and a refractive value measuring light beam can be aligned to an eye to be examined even if the examiner does not at all perform the alignment operation.

It is another object of the present invention to provide an ophthalmic apparatus requiring no sliding stand in which alignment can be simply accomplished by displacing the angle or the position of a light reflecting member and without moving the entire apparatus.

It is a further object of the present invention to provide an ophthalmic apparatus in which a member for changing over tile optical paths of the right and left eyes is used also as a member for alignment adjustment to thereby make the apparatus compact and misjudgment to prevent a mistake in determining whether the right or left eye is being detected.

It is still a further object of the present invention to provide an ophthalmic apparatus which eliminates the necessity of a chin receiving stand and which is not affected by the corneal reflection of an illuminating light source in the room.

DESCRIPTION OF THE PREFERRED EMBODIMENTS

Figure 1:
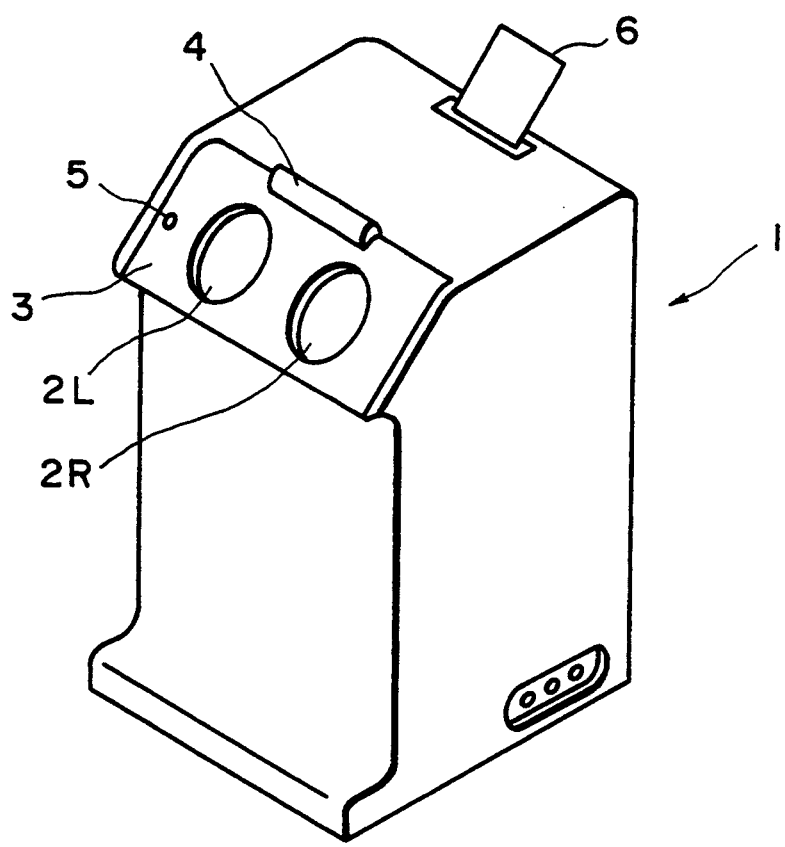
FIG. 1 shows the appearances of an eye-refractometer.

The present invention will hereinafter be described in detail with respect to an embodiment thereof shown in the drawings.

Referring to FIG. 1 which shows the outside of an eye-refractometer according to the present invention, a panel 3 as a face placing portion provided with binocular openings 2L and 2R is provided on the examinee's side of the eye-refractometer body 1, a forehead pad 4 and a nearby sensor 5 are mounted on the upper portion of the panel 3, and a printer 6 for outputting a measured value is installed on top of the eye-refractometer body 1.

Figure 2:
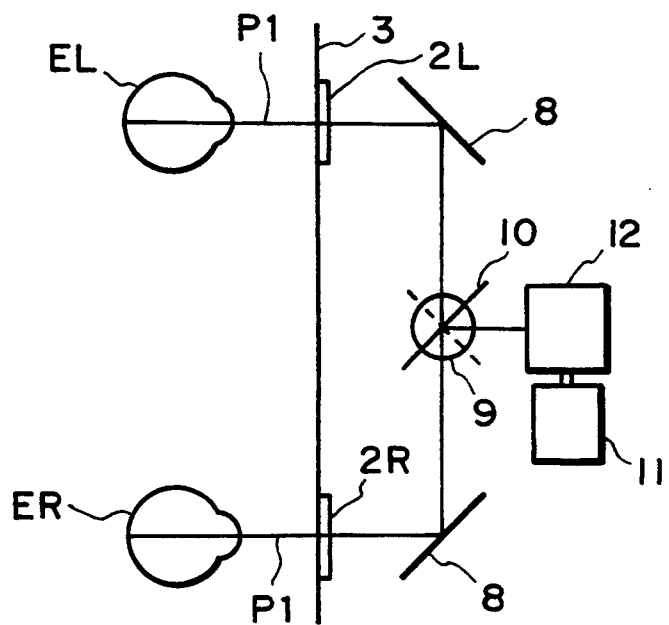
FIGS. 2 and 3 show optical paths.
Figure 3:
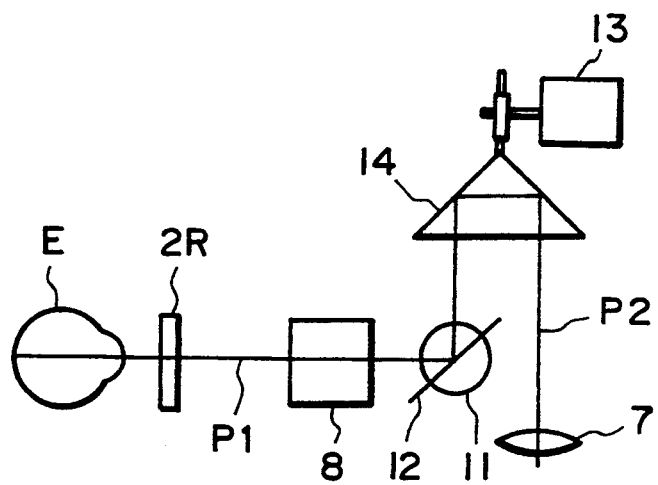

FIG. 2 shows a view of an optical path of an alignment optical system in the eye-refractometer body 1 seen from above, and FIG. 3 shows a view of an optical path of the alignment optical system seen from the side. On two optical paths P1 leading from the two left and right eye openings 2L and 2R to a lens 7 constituting a part of a measuring optical system, there are provided two visible light transmitting mirrors 8 reflecting infrared light and transmitting visible light therethrough. A position adjustment mirror 10 is provided so as to make the two optical paths P1 coincident with each other and change over the optical path toward one of the two visible light transmitting mirrors 8. The position adjustment mirror 10 is driven by a stepping motor 9 and is used to effect alignment in the horizontal direction. There are further provided a position adjustment mirror 12 driven by a stepping motor 11 to effect alignment in the vertical direction, and a prism 14 driven by a stepping motor 13 to effect alignment in the direction of the optic axis.

Figure 4:
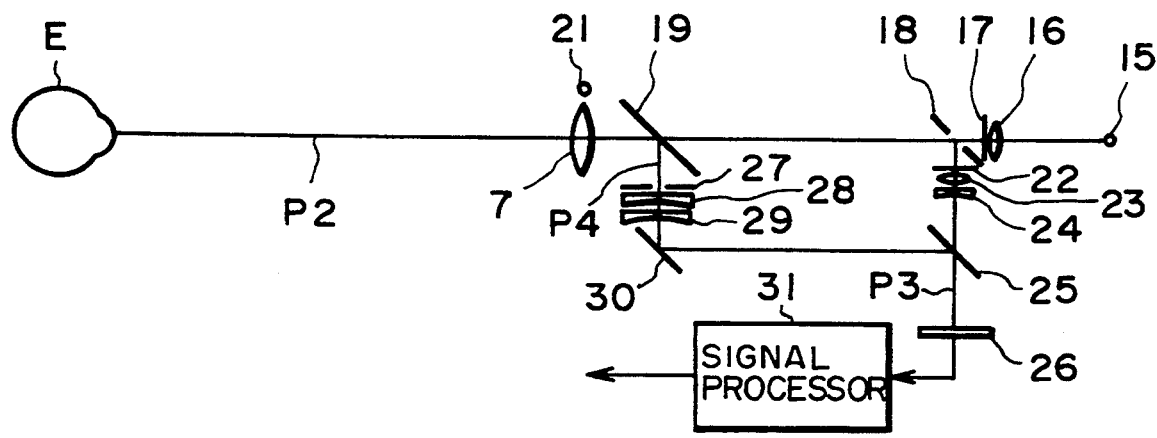
FIG. 4 shows the optical path of a measuring optical system.
Figure 5:
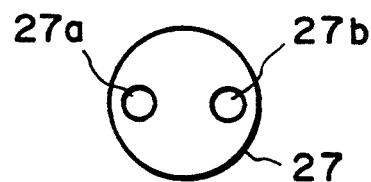
FIG. 5 is a front view of a two-aperture diaphragm.

Referring now to FIG. 4 which shows the construction of a refract ion measuring optical system as an eye examining system in which an alignment optical system is omitted, on the optic axis P2 between an eye E to be examined and a light source 15 for measurement of eye refraction, there are provided a lens 16, a central aperture stop 17, an apertured mirror 18, a dichroic mirror 19 and a lens 7 in succession from the light source 15 side. At a predetermined location near the lens 7, a single light source 21 for alignment is installed off the optic axis P2. Also, on an optic axis P3 bent by the apertured mirror 18, there are arranged, in succession from the apertured mirror 18 side, a six-aperture diaphragm 22 having six openings, a lens 23, a separating prism 24 comprised of six wedge prisms, a dichroic mirror 25 and a photoelectric sensor 26 comprising a two-dimensional CCD. On an optic axis P4 bent by the dichroic mirror 19, there are provided, in succession from the dichroic mirror 19 side, a two-aperture diaphragm 27 having two openings 27a and 27b shown in FIG. 5, a wedge prism 28 comprising two wedge prisms, a lens 29 and a mirror 30. The reflected light from the mirror 30 may enter the dichroic mirror 25 and may be further reflected toward the photoelectric sensor 26. The output of the photoelectric sensor 26 is connected to a signal processor 31, the output of which is connected to a monitor and a printer, not shown, and the stepping motors 9, 11 and 13. The light source 15 and the light source 21 are made conjugate with the photoelectric sensor 26 through eye fundus reflection and corneal reflection, respectively.

Figure 6:
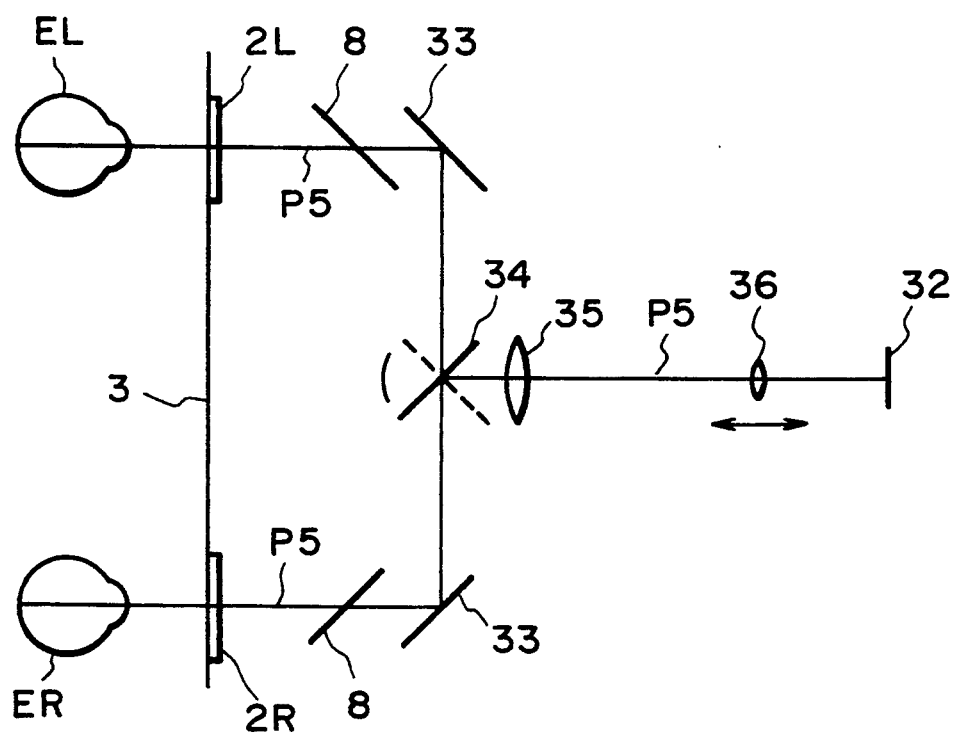
FIG. 6 shows the optical paths of a fixation target optical system.

Referring to FIG. 6 which shows the optical paths of a fixation target optical system, a part of two optical paths P5 leading from the binocular openings 2L and 2R to a fixation target 32 is made common to the optical path P1 shown in FIG. 2, and a deflecting mirror 33 is disposed rearwardly of the visible light transmitting mirror 8, and further, along the optical paths P5 aggregated to one, there are provided a movable mirror 34 driven by a stepping motor, not shown, for changing over the left and right eye optical paths (which mirror is operatively associated with the position adjustment mirror 10 of FIG. 2), a lens 35 and a lens 36.

When during measurement, the examinee looks into the eye-refractometer body 1 through the binocular openings 2L and 2R with his left and right eyes EL and ER to be examined with his forehead bearing against the forehead pad 4, it is detected by the nearby sensor 5 that the examinee is looking into the eye-refractometer body, and preparation for measurement is started. With the examinee's gaze fixed on the fixation target 32 presented by the fixation target optical system, auto alignment is effected in the alignment optical system shown in FIGS. 2 to 4, whereafter measurement of the eye refractive value is effected by an eye refractive power measuring optical system as an eye examining optical system. This process will hereinafter be described in detail.

First, in the fixation target optical system shown in FIG. 6, the image of the fixation target 32 irradiated with a light source, not shown, passes through the lens 36 and the lens 35, and thereafter is reflected by the movable mirror 34 toward the mirror 33 provided forwardly of the left or right eye EL or ER to be measured, and is further reflected by the mirror 33, and then passes through the visible light transmitting mirror 8 and the binocular opening 2L or 2R to the eye EL or ER to be examined and therefore, the examinee's gaze can be fixed in the fixation target 32 with his eye EL or ER to be measured. The focusing of the fixation target 32 is accomplished by adjusting the lens 36 and the lens 35 in accordance with the visibility of the eye EL or ER to be examined.

Figure 7:
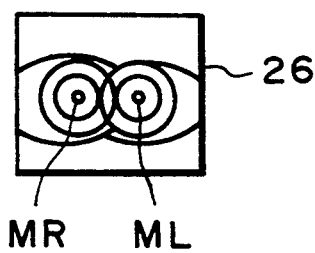
FIG. 7 shows the images of front eye parts on a photoelectric sensor.

Next, during alignment, a light beam emitted from the single alignment light source 21 arrives at the eye EL or ER to be measured via the alignment optical system of FIGS. 2 and 3 including the position adjustment mirror 10 capable of changing over the left and right eye optical paths. Then, the light reflected by the cornea returns along the same optical path and is reflected toward the optic axis P4 by the dichroic mirror 19 shown in FIG. 4, and is separated into two by the two-aperture diaphragm 27 and the wedge prism 28, and thereafter is reflected by the mirror 30 and the dichroic mirror 25 via the lens 29 and the reflected images ML and MR of the corneas are projected onto the photoelectric sensor 26 as shown in FIG. 7. The signals of the reflected images ML and MR of the corneas are processed by the signal processor 31, and the positional information in the plane perpendicular to the optic axis P3 can be obtained from the positions of the centers of gravity of the reflected images ML and MR and the positional information in the direction of the optic axis P3 can be obtained from the spacing between the reflected images ML and MR. From these two kinds of information, the position adjustment mirrors 10, 12 and the prism 14 are moved, whereby alignment in the horizontal direction, the vertical direction and the longitudinal direction can be automatically accomplished. That is, by the driving of the stepping motor 9, the position adjustment mirror 10 is moved to shift the light beam to the left and right and make it coincident with the pupil position, and by the position adjustment stepping motor 11, the mirror 12 is moved to accomplish alignment in the vertical direction, and by the stepping motor 13, the prism 14 is moved to accomplish alignment in the direction of the optic axis. When the alignment is completed, measurement of eye refractive power is automatically started.

Figure 8:
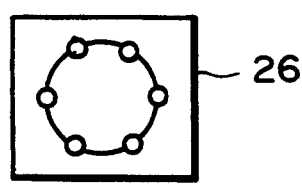
FIG. 8 illustrates a light beam projected onto the photoelectric sensor.

When measurement of the eye refractive value is to be effected, the infrared light beam emitted from the light source 15 in the measuring optical system shown in FIG. 4 passes through the lens 16, the central aperture stop 17, the apertured mirror 18, the dichroic mirror 19 and the lens 7 on the optic axis P2, and in the alignment optical system wherein the alignment adjustment of FIGS. 2 and 3 is effected, enters the position adjustment mirror 10 through via position adjustment mirror 12, and is reflected to the visible light transmitting mirror 8 on the eye EL or ER side to be measured by the position adjustment mirror 10, and further enters the eye EL or ER to be examined via the binocular opening 2L or 2R, and is reflected by the eye fundus or the cornea, whereafter the reflected light returns to the measuring optical system along the same optical path P1. On the apertured mirror 18, the reflected light is reflected toward the optic axis P3, is separated from the; optic axis P3 by the separating prism 24 via the six-aperture diaphragm 22 and the lens 23, and projects six optical images as shown in FIG. 8 onto the photoelectric sensor 26 via the dichroic mirror 25 and therefore, the positional signals of these optical images on the photoelectric sensor 26 are processed by the signal processor 31 to thereby effect measurement of the eye refractive value.

In the above-described embodiment, the light source 15 for measurement and the light source 21 for alignment are discrete from each other, but alternatively, alignment can also be effected by the use of the light source 15, and further, although the photoelectric sensor 26 is used in common for alignment and measurement of the refractive value, discrete sensors may be used. Also, in the above-described embodiment, the reflected light from the cornea is detected by the photoelectric sensor 26 and alignment is effected on the basis of the position of the corneal reflected image, but alternatively, the pupil position of the front eye part image may be detected to thereby effect alignment. Further, in the above-described embodiment, alignment is effected with only the mirrors 10, 12 and prism 14 of the alignment optical system moved and therefore, alignment can be accomplished at a high speed. When the entire optical system is compact, alignment can be effected with the entire apparatus moved.

As described above, according to the present invention, when during the measurement of the refractive value, the examinee looks into the binocular openings, his eyes are aligned with predetermined positions irrespective of the size of his face, and auto alignment can be accomplished with the positions of the eyes to be examined being detected on the photoelectric sensor, and also the eyes to be examined become proximate to the binocular openings and therefore, the light beam from the illuminating light source in the room is not reflected by the cornea and highly accurate measurement of the refractive value becomes possible and further, a chin supporting stand and a sliding stand become unnecessary and thus, the structure of the apparatus becomes simple.

I claim:

1. An ophthalmic apparatus having:
   an eye examining system adapted to be positioned opposed to an eye to be examined for detecting information of the eye to be examined;
   a face supporting portion opposed to said eye examining system for supporting an examinee's face thereon, said face supporting portion being provided with apertures for the examinee to look into;
   a projection optical system for projecting the image of the surface of the front eye part of one of the examinee's eyes looking into one of the apertures onto an image plane;
   photoelectric detecting means provided on the image plane of said projection optical system; and
   aligning means for aligning said eye examining system with the eye to be examined looking into one of the apertures on the basis of the output of said photoelectric detecting means when said face supporting portion is stationary,
   wherein the detecting of information with said eye examining system and the projecting by said projection optical system are performed through one of the apertures.

2. An ophthalmic apparatus according to claim 1, wherein said eye examining system comprises a light reflecting member, wherein said aligning means effects alignment by displacing at least one of the position and the angle of said light reflecting member of said eye examining system.

3. An ophthalmic apparatus according to claim 2, wherein said light reflecting member effects alignment by varying the angle of a light reflecting member for effecting alignment in a direction perpendicular to the optic axis of the eye to be examined, and displacing a light reflecting member for effecting alignment in the direction of the optic axis.

4. An ophthalmic apparatus according to claim 1, further comprising an illuminating light source for illuminating the front eye part of the eye to be examined.

5. An ophthalmic apparatus according to claim 4, wherein said photoelectric detecting means is a light position sensor and detects the position of the corneal reflected image of said illuminating light source.

6. An ophthalmic apparatus according to claim 5, further comprising a stop for extracting two separated light beams in the optical path of said imaging optical system.

7. An ophthalmic apparatus according to claim 6, further comprising a prism for separating the images by the two light beams separated by said stop in the optical path of said imaging optical system.

8. An ophthalmic apparatus according to claim 7, wherein said stop extracts two corneal reflected images and said prism separates the two corneal reflected images, and wherein the spacing between the separated corneal reflected images and the bisected position of the separated corneal reflected images are detected as the output of said light position sensor, and wherein said aligning means effects alignment so as to correct misalignment in the direction of the optic axis and to correct misalignment in a direction perpendicular to the optic axis.

9. An ophthalmic apparatus according to claim 5, wherein said eye examining system comprises a light reflecting member, and wherein said aligning means effects alignment by displacing at least one of the position and the angle of said light reflecting member in said eye examining system.

10. An ophthalmic apparatus according to claim 9, wherein said light reflecting member effects alignment by displacing the angle of a light reflecting member for effecting alignment in a direction perpendicular to the optic axis of the eye to be examined, and displacing the position of a light reflecting member for effecting alignment in the direction of the optic axis.

11. An ophthalmic apparatus according to claim 10, wherein said photoelectric detecting means is a light position sensor and detects the position of the corneal reflected image of said illuminating light sensor.

12. An ophthalmic apparatus according to claim 11, further comprising a stop for extracting two separated light beams in the optical path of said imaging optical system.

13. An ophthalmic apparatus according to claim 12, further comprising a prism for separating the images by the two light beams separated by said stop in the optical path of said imaging optical system.

14. An ophthalmic apparatus according to claim 13, wherein said stop extracts two corneal reflected images and said prism separates the two corneal reflected images, and wherein the spacing between the separated corneal reflected images and the bisected position of the separated corneal reflected images are detected as the output of said light position sensor, and wherein said aligning means effects alignment so as to correct misalignment in the direction of the optic axis and to correct misalignment in a direction perpendicular to the optic axis.

15. An ophthalmic apparatus according to claim 5, wherein said photoelectric detecting means is used also as a sensor of said eye examining system for detecting the information of the eye to be examined.

16. An ophthalmic apparatus according to claim 5, wherein said illuminating light source for alignment is used also as the eye examining light source of said eye examining system.

17. An ophthalmic apparatus according to claim 5, wherein the information of the eye to be examined is the eye refractive power of the eye to be examined.

18. An ophthalmic apparatus according to claim 5, further comprising a change-over mirror in the optical path of said projection optical system, and wherein said change-over mirror is rotated to change over the left and right eye optical paths.

19. An ophthalmic apparatus according to claim 18, wherein said change-over mirror is used also as a member for alignment.

20. An ophthalmic apparatus according to claim 19, wherein said change-over mirror is used also as a mirror for alignment in the horizontal direction, and further comprising discrete members for alignment in the vertical direction and the longitudinal direction.

21. An ophthalmic apparatus according to claim 4, wherein said illuminating light source for alignment is used also as the eye examining light source of said eye examining system.

22. An ophthalmic apparatus according to claim 1, wherein said photoelectric detecting means is used also as a sensor of said eye examining system for detecting the information of the eye to be examined.

23. An ophthalmic apparatus according to claim 1, wherein the information of the eye to be examined is the eye refractive power of the eye to be examined.

24. An ophthalmic apparatus according to claim 1, further comprising a change-over mirror in the optical path of said projection optical system, and wherein said change-over mirror is rotated to change over the left and right eye optical paths.

25. An ophthalmic apparatus according to claim 24, wherein said change-over mirror is used also as a member for alignment.

26. An ophthalmic apparatus according to claim 25, wherein said change-over mirror is used also as a mirror for alignment in the horizontal direction, and further comprising discrete members for alignment in the vertical direction and the longitudinal direction.

27. An apparatus according to claim 1, wherein said eye examining system projects a light beam for examination toward at least one of the eyes to be examined and wherein said aligning means causes an alignment such that the light beam for examination from the eye examining system is directed to at least one of the eyes to be examined.

28. An ophthalmic apparatus comprising:
a an eye examining system adapted to be positioned opposed to an eye to be examined for detecting information of the eye to be examined;
a face supporting portion opposed to said eye examining system for supporting an examinee's face thereon, said face supporting portion being provided with an aperture for examinee to look into;
a projection optical system for projecting the image of the surface of the front eye part of one of the examinee's eyes looking into the aperture onto an image plane; and
aligning means for aligning said eye examining system with the eye to be examined looking into the aperture when said face supporting portion is stationary,
wherein the detecting of information with said eye examining system and the projecting by said projection optical system are performed through the aperture.

29. An apparatus according to claim 28, wherein said eye examining system projects a light beam for examination toward the eye to be examined and wherein said aligning means causes an alignment such that the light beam for examination from the eye examining system is directed to the eye to be examined.

30. An ophthalmic apparatus comprising:
a main body;
an eye examining system adapted to be positioned opposed to an eye to be examined for detecting information of the eye to be examined, said eye examining system being disposed in said main body;
a face supporting portion, disposed on said main body and opposed to said eye examining system, for supporting an examinee's face thereon, said face supporting portion being provided with an aperture for examinee to look into said main body;
a projection optical system for projecting the light from the surface of the front eye part of one of the examinee's eyes looking into the aperture onto an image plane, the light projected by said projecting optical system being used for aligning said eye examining system with the eye to be examined; and
aligning means for aligning said eye examining system with the eye to be examined looking into the aperture under the condition that said main body is stationary relative to the eye to be examined,
wherein the detecting of information with said eye examining system and the projecting by said projection optical system are performed through the aperture.

* * * * *

UNITED STATES PATENT AND TRADEMARK OFFICE
CERTIFICATE OF CORRECTION

PATENT NO. : 5,371,558
DATED : December 6, 1994
INVENTOR(S) : YOSHIMI KOHAYAKAWA It is certified that error appears in the above-indentified patent and that said Letters Patent is hereby corrected as shown below:

COLUMN 1

Line 32, "process" should read --processes--.
    Line 59, "tile" should read --the--.

COLUMN 2

Line 51, "refract ion" should read --refraction--.

COLUMN 4

Line 31, "through via" should read -- via--.

Signed and Sealed this

Sixteenth Day of May, 1995

Attest:

BRUCE LEHMAN

*Attesting Officer*      *Commissioner of Patents and Trademarks*